US006391607B1

(12) United States Patent
Lazarus et al.

(10) Patent No.: US 6,391,607 B1
(45) Date of Patent: *May 21, 2002

(54) HUMAN DNASE I HYPERACTIVE VARIANTS

(75) Inventors: Robert A. Lazarus, Millbrae; Clark Qun Pan, San Francisco, both of CA (US)

(73) Assignee: Genentech, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/663,831

(22) Filed: Jun. 14, 1996

(51) Int. Cl.$^7$ .............................. C12N 9/00; C12N 9/14; C12N 9/22; A61K 38/46

(52) U.S. Cl. ....................... 435/199; 435/183; 435/195; 435/196; 424/94.6

(58) Field of Search ................................. 435/196, 199; 536/23.2; 424/94.6; 935/10, 14

(56) References Cited

FOREIGN PATENT DOCUMENTS

| WO | WO 90/07572 | 7/1990 |
|---|---|---|
| WO | WO 93/25670 | 12/1993 |
| WO | WO 94/10567 | 5/1994 |
| WO | WO 94/22465 | 10/1994 |
| WO | WO 96/26278 | 8/1996 |
| WO | WO 96/26279 | 8/1996 |

OTHER PUBLICATIONS

Aitken et al., "Recombinant Human DNase Inhalation in Normal Subjects and Patients With Cystic Fibrosis" *Journal of the American Medical Assn.* 267(14):1947–1951 (1992).
Bryson et al., "Dornase Alfa: A Review of its Pharmacological Properties and Therapeutic Potential in Cystic Fibrosis" *Drugs* 48(6):894–906 (1994).
Doherty et al., "Mutagenesis of the DNA Binding Residues in Bovine Pancreatic DNase1: an Investigation Into the Mechanism of Sequence Discrimination by a Sequence Selective Nuclease" *Nucleic Acids Research* 19(22):6129–6132 (1991).
Fitch et al., "Optimal Sequence Alignments" *Proc. Natl. Acad. Sci. USA* 80:1382–1386 (Mar. 1983).
Fuchs et al., "Effect of Aerosolized Recombinant Human DNase on Exacerbations of Respiratory Symptoms and on Pulmonary Function in Patients with Cystic Fibrosis" *New England J. of Medicine* 331(10):637–642 (1994).
Goldschmidt–Clermont et al., "Distinct Sites on the G–actin Molecule Bind Group–specific Component and Deoxyribonuclease I" *Biochemical Journal* 228:471–477 (1985).
Hitchcock et al., "Depolymerization of F–actin by Deoxyribonuclease I" *Cell* 7:531–542 (Apr. 1976).

Houmeida et al., "Localization of a Vitamin–D–binding Protein Interaction Site in the COOH–terminal Sequence of Actin" *European Journal of Biochemistry* 203:499–503 (1992).
Hubbard et al., "A Preliminary Study of Aerosolized Recombinant Human Deoxyribonuclease I in the Treatment of Cystic Fibrosis" *New England J. of Medicine* 326(12):812–815 (Mar. 19, 1992).
Jamney, P., "A Torsion Pendulum for Measurement of the Viscoelasticity of Biopolymers and Its Application to Actin Networks" *J. Biochem. Biophys. Methods* 22:41–53 (1991).
Janmey et al., "Viscoelasticity of F–Actin and F–Actin/Gelsolin Complexes" *Biochemistry* 27:8218–8226 (1988).
Kabsch et al., "Atomic Structure of the Actin: DNase I Complex" *Nature* 347:37–44 (1990).
Kabsch et al., "Structure and Function of Actin" *Ann. Rev. Biophys. Biomol. Struct.,* Engelman et al. vol. 21:49–76 (1992).
Kreuder et al., "Isolation, Characterisation and Crystallization of Deoxyribonuclease I from Bovine and Rat parotid Gland and It's Interaction With Rabbit Skeletal Muscle Actin" *European Journal of Biochemistry* 139:389–400 (1984).
Kunitz, M., "Crystalline Desoxyribonuclease: I. Isolation and General Properties" *J. Gen. Physiol.* 33:349–362 (1950).
Kunitz, M., "Crystalline Desoxyribonuclease: II. Digestion of Thymus Nucleic Acid (Desoxyribonucleic Acid)" *J. Gen. Physiol.* 33:363–377 (1950).
Rudinger (1976) Characteristics of the amino acids as components of a peptide hormone sequence. In: Peptide Hormones. Ed. J. A. Parsons. University Park Press, Baltimore, MD. pp. 1–7, Jun. 1976.
Ngo et al. (1994) Computational complexity, protein structure prediction, and the ILevinthal paradox. In: The Protein Folding Problem and Tertiary Structure Prediction. Eds. Merz et al. Birkhauser et al. Boston, MA. pp. 491–495, Jan. 1994.
Thornton et al. (1995) Protein Engineering: Editoral Overview. Current Opinion in Biotechnology 6(4): 367–369, Aug. 1995.
Wallace (1993) Understanding cytochrome c function: engineering protein structure by semisynthesis. The FASEB Journal 7: 505–515, Apr. 1993.
Shak et al. Proc. Natl. Acad. Sci., USA., 1990, vol. 87:9188–9192.

(List continued on next page.)

*Primary Examiner*—Ponnathapu Achutamurthy
*Assistant Examiner*—Manjunath N. Rao
(74) *Attorney, Agent, or Firm*—Sean A. Johnston; David W Evans

(57) ABSTRACT

The present invention relates to amino acid sequence variants of human DNase I that have increased DNA-hydrolytic activity. The invention provides nucleic acid sequences encoding such hyperactive variants, thereby enabling the production of these variants in quantities sufficient for clinical use. The invention also relates to pharmaceutical compositions and therapeutic uses of hyperactive variants of human DNase I.

10 Claims, 4 Drawing Sheets

OTHER PUBLICATIONS

Mannherz et al. Biochem. J., 1982, vol. 207:305–313.

Sheterline et al. *Prot. Profile* 1:1–121 (1994).

Sinicropi et al., "Colorimetric Dtermination of DNase I Activity with a DNA–Methyl Green Substrate" *Analytical Biochemistry* 222:351–358 (1994).

Suck et al., "Structure of DNase I at 2.0 A Resolution Suggests a Mechanism for Binding To and Cutting DNA" *Nature* 321:620–625 (Jun. 1986).

Suck et al., "Structure refined to 2A of a Nicked DNA Octanucleotide Complex with DNase I" *Nature* 332:464–468 (1988).

Suck et al., "Three–dimensional Structure of Bovine Pancreatic DNase I at 2.5 A Resolution" *EMBO Journal* 3(10):2423–2430 (1984).

Vasconcellos et al., "Reduction in Viscosity of Cystic Fibrosis Sputum in Vitro by Gelsolin" *Science* 263:969–971 (Feb. 1994).

Weber et al., "DNase I Increases the Rate Constant of Depolymerization at the Pointed (–) End of Actin Filaments" *Biochemistry* 33(16):4780–4786 (1994).

Weston and Suck, "X–ray Structures of Two Single–Residue Mutants of DNase I: H134Q and Y76A" *Protein Engineering* 6(4):349–357 (1993).

Weston et al., "X–ray Structure of the DNase I–d (GGTATACC)2 Complex at 2.3 A Resolution" *J. Mol. Biol.* 226:1237–1256 (1992).

Worrall et al., "The Chemical Synthesis of a Gene Coding for Bovine Pancreatic DNase I and Its Cloning and Expression in *Escherichia coli*" *Journal Biological Chemistry* 265(35):21889–21895 (Dec. 1990).

Liao, Ta Hsiu et al., "Bovine pancreatic deoxyribonuclease A. Isolation of cyanogen bromide peptides, complete covalent structure of the polypeptide chain" *Journal of Biological Chemistry* 267(11):7957 (1992).

Suck, D., "DNA recognition by DNase I" *J. Mol. Recognit.* 7(2):65–70 (Jun. 1994).

Kurnick, N. B., "The Determination of Desoxyribonuclease Activity by Methyl Green; Application to Serum" *Arch. Biochem.* 29:41–53 (1950).

Lacks, S., "Deoxyribonuclease I in Mammalian Tissues" *Journal of Biological Chemistry* 256 (6) :2644–2648 (1981).

Lahm et al., "DNase I–induced DNA Conformation" *Journal Molecular Biology* 221:645–667 (1991).

Lazarides et al., "actin is the Naturally Occurring Inhibitor of Deoxyribonuclease I" *Proc. Natl. Acad. Sci. USA* 71 (12) : 4742–4746 (Dec. 1974).

Liao et al., "Bovine Pancreatic Deoxyribonuclease A" *Journal of Biological Chemistry* 248 (4) :1489–1495 (1973).

Lourenco et al., "Clinical Aerosols. II. Therapeutic Aerosols" *Arch. Intern. Med.* 142:2299–2308 (Dec. 1982).

Mannherz et al., "The Inhibition of Bovine and Rat Parotid Deoxyribonuclease I by Skeletal Muscle Actin" *Biochemical Journal* 207:305–313 (1982).

Mannherz et al., "The Interaction of Bovine Pancreatic Deoxyribonuclease I and Skeletal Muscle Actin" *European Journal of Biochemistry* 104:367–379 (1980).

Mannherz et al., "A Specific 1:1 G–Actin:DNAse I Complex Formed by the Action of DNAse I on F–Actin" *FEBS Letter* 60 (1) : 34–38 (Dec. 1975).

Matsudaira et al., "Pieces in the Actin–severing Protein Puzzle" *Cell* 54:139–140 (Jul. 1988).

McLeod et al., "Interactions among Serum Vitamin D Binding Protein, Monomeric Actin, Profilin, and Profilactin" *Journal of Biological Chemistry* 264 (2) : 1260–1267 (Jan. 1989).

Moore, S., "Pancreatic DNase" *The Enzymes*, Boyer, Ph. D., New York, NY:Academic Press vol. XIV:281–296 (1981).

Mornet et al., "Proteolysis and Structure of Skeletal Muscle Actin" *Proc. Natl. Acad. Sci. USA* 81:3680–3684 (Jun. 1984).

Needleman et al., "A General Method Applicable to the Search for Similarities in the Amino Acid Sequence of Two Proteins" *J. Mol. Biol.* 48:443–453 (1970).

Newman et al., "Presence of Oligomers at Subcritical Actin Concentrations" *Biochemistry* 24:1538–1544 (1985).

Oefner et al., "Crystallographic Refinement and Structure of DNase I at 2 A Resolution" *Journal Molecular Biology* 192:605–632 (1986).

Pardee et al. "Purification of Muscle Actin" *Methods in Enzymology* 85:164–181 (1982).

Pinder et al., "Investigation of the Actin–Deoxyribonuclease I Interaction Using a Pyrene–conjugate Actin Derivative" *Biochemistry* 21:4886–4890 (1982).

Ranasinha et al., "Efficacy and Safety of Short–term Administration of Aerosolised Recombinant Human DNase I in Adults with Stable Stage Cystic Fibrosis" *Lancet* 342 (8865) : 199–202 (Jul. 24, 1993).

Shak et al., "Recombinant Human DNase I Reduces the Viscosity of Cystic Fibrosis Sputum" *Proc. Natl. Acad. Sci. USA* 87 (23) :9188–9192 (Dec. 1990).

Figure 1

Human Mature DNase I

```
         10        20        30        40        50
LKIAAFNIQTFGETKMSNATLVSYIVQILSRYDIALVQEVRDSHLTAVGK 60        70        80        90       100
LLDNLNQDAPDTYHYVVSEPLGRNSYKERYLFVYRPDQVSAVDSYYYDDG 110       120       130       140       150
CEPCGNDTFNREPAIVRFFSRFTEVREFAIVPLHAAPGDAVAEIDALYDV 160       170       180       190       200
YLDVQEKWGLEDVMLMGDFNAGCSYVRPSQWSSIRLWTSPTFQWLIPDSA 210       220       230       240       250
DTTATPTHCAYDRIVVAGMLLRGAVVPDSALPFNFQAAYGLSDQLAQAIS

260
DHYPVEVMLK
```

Figure 2

Plasmid DNA Digestion Assays

| DNase I Variants | Linear DNA Digestion Assay<br>Relative Linear DNA Digestion Activity | Supercoiled DNA Digestion Assay<br>L/R ratio | Relative Nicking Activity |
|---|---|---|---|
| native human DNase I | 1.0 ± 0.1 | 1.0 | 1.0 ± 0.0 |
| Q9R | 3.5 ± 0.4 | 2.3 | 3.4 ± 0.5 |
| E13K | 3.9 ± 0.1 | | |
| E13R | 6.0 ± 0.5 | 5.4 | 2.2 ± 0.0 |
| T14K | 4.2 ± 0.1 | 4.7 | 2.9 ± 0.8 |
| T14R | 3.5 ± 0.7 | | |
| H44K | 2.0 ± 0.4 | 2.3 | 1.8 ± 0.3 |
| H44R | 3.6 ± 0.5 | | |
| N74K | 6.0 ± 0.1 | 4.7 | 7.3 ± 1.0 |
| N74R | 4.1 ± 0.8 | | |
| S75K | 1.5 ± 0.2 | | |
| T205K | 4.7 ± 0.2 | 5.4 | 2.8 ± 0.7 |
| T205R | 2.3 ± 0.3 | | |
| E13R:N74K | 26.7 ± 4.1 | 12.3 | 6.9 ± 1.6 |
| Q9R:E13R:N74K | 38.3 ± 1.2 | 16.5 | 6.3 ± 2.2 |
| E13R:N74K:T205K | 19.5 ± 6.4 | | |
| Q9R:E13R:N74K:T205K | 30.5 ± 7.5 | | |

All data is normalized to native human DNase I.

Figure 3

DNA Hyperchromicity Assay

| DNase I Variants | $1/K_m$ | $V_{max}$ | $V_{max}/K_m$ |
|---|---|---|---|
| native human DNase I | 1.0 ± 0.1 | 1.0 ± 0.1 | 1.0 |
| Q9R | 0.9 ± 0.2 | 2.8 ± 0.4 | 2.6 |
| E13K | 2.5 ± 0.4 | 1.8 ± 0.1 | 4.5 |
| E13R | 4.3 ± 1.4 | 1.5 ± 0.1 | 6.5 |
| T14K | 2.3 ± 0.9 | 1.1 ± 0.2 | 2.5 |
| T14R | 2.1 ± 0.8 | 0.7 ± 0.1 | 1.5 |
| H44K | 2.3 ± 0.5 | 1.1 ± 0.1 | 2.5 |
| H44R | 1.7 ± 0.2 | 1.0 ± 0.1 | 1.7 |
| N74K | 0.4 ± 0.2 | 5.5 ± 1.3 | 2.3 |
| N74R | 2.6 ± 0.8 | 3.1 ± 0.3 | 8.1 |
| S75K | 18.5 ± 2.0 | 0.4 ± 0.1 | 7.4 |
| T205K | 2.4 ± 0.8 | 2.1 ± 0.4 | 5.0 |
| T205R | 3.0 ± 1.2 | 1.0 ± 0.1 | 3.0 |
| E13R:N74K | 5.0 ± 1.7 | 5.3 ± 0.5 | 26.5 |
| Q9R:E13R:N74K | 4.9 ± 1.3 | 7.0 ± 0.4 | 34.3 |
| E13R:N74K:T205K | 5.0 ± 1.9 | 6.3 ± 0.6 | 31.5 |
| Q9R:E13R:N74K:T205K | 5.6 ± 1.4 | 3.8 ± 0.3 | 21.3 |

All data is normalized to native human DNase I.

HUMAN DNASE I HYPERACTIVE VARIANTS

FIELD OF THE INVENTION

The present invention is related to results obtained from research on human deoxyribonuclease I (DNase I), a phosphodiesterase that is capable of hydrolyzing polydeoxyribonucleic acid. It relates generally to modified (variant) forms of human DNase I having increased DNA-hydrolytic activity and their preparation by recombinant DNA methods, to pharmaceutical compositions by which their utility can be exploited clinically, and to methods of using these DNase I variants and compositions thereof.

BACKGROUND OF THE INVENTION

DNase I is a phosphodiesterase capable of hydrolyzing polydeoxyribonucleic acid. DNase I has been purified from various species to various degrees.

Bovine DNase I has been extensively studied biochemically. See e.g., Moore, in *The Enzymes* (Boyer, P. D., ed), pp. 281–296, Academic press, New York (1981). The complete amino acid sequence for bovine DNase I is known (Liao, et al., J. Biol. Chem. 248:1489–1495 (1973); Oefner, et al., J. Mol. Biol. 192:605–632 (1986); Lahm, et al., J. Mol. Biol. 221:645–667 (1991)), and DNA encoding bovine DNase I has been cloned and expressed (Worrall, et al., J. Biol. Chem 265:21889–21895 (1990)). The structure of bovine DNase I has been determined by X-ray crystallography. Suck, et al., EMBO J. 3:2423–2430 (1984); Suck, et al., Nature 321:620–625 (1986); Oefner, et al., J. Mol. Biol. 192:605–632 (1986); Weston, et al., J. Mol. Biol. 226:1237–1256 (1992).

DNA encoding human DNase I has been isolated and sequenced and that DNA has been expressed in recombinant host cells, thereby enabling the production of human DNase I in commercially useful quantities. Shak, et al., Proc. Nat. Acad. Sci. 87:9188–9192 (1990).

DNase I has a number of known utilities and has been used for therapeutic purposes. Its principal therapeutic use has been to reduce the viscoelasticity of pulmonary secretions (mucus) in such diseases as pneumonia and cystic fibrosis (CF), thereby aiding in the clearing of respiratory airways. See e.g., Lourenco, et al., Arch. Intern. Med. 142:2299–2308 (1982); Shak, et al., Proc. Nat. Acad. Sci. 87:9188–9192 (1990); Hubbard, et al., New Engl. J. Med. 326:812–815 (1992); Fuchs, et al., New Engl. G. Med. 331:637–642 (1994); Bryson, et al., Drugs 48:894–906 (1994). Mucus also contributes to the morbidity of chronic bronchitis, asthmatic bronchitis, bronchiectasis, emphysema, acute and chronic sinusitis, and even the common cold.

The pulmonary secretions of persons having such diseases are complex materials, that include mucus glycoproteins, mucopolysaccharides, proteases, actin, and DNA. Some of the materials in pulmonary secretions are released from leukocytes (neutrophils) that infiltrate pulmonary tissue in response to the presence of microbes (e.g., strains of Pseudomonas, Pneumococcus, or Staphylococcus bacteria) or other irritants (e.g., tobacco smoke, pollen). In the course of reacting with such microbes or irritants, the leukocytes may degenerate and release their contents, which contribute to the viscoelasticity of the pulmonary secretions.

The ability of DNase I to reduce the viscoelasticity of pulmonary secretions has been ascribed to its enzymatic degradation of the large amounts of DNA released by neutrophils. Shak, et al., Proc. Nat. Acad. Sci. 87:9188–9192 (1990); Aitken, et al., J. Am. Med. Assoc. 267:1947–1951 (1992).

The present invention is based in part on research by the inventors to study the enzymatic activity of human DNase I. This research involved the design and synthesis of various human DNase I variants, and the assay of these variants to assess their ability to hydrolyze DNA in vitro. The inventors have identified for the first time a class of human DNase I variants, termed hyperactive variants, that have increased DNA-hydrolytic activity and that are less susceptible to inhibition by sodium chloride, as compared to native human DNase I.

Because of their increased DNA-hydrolytic activity, the hyperactive variants also have increased mucolytic activity and are more effective than native human DNase I in degrading (digesting) DNA generally. Because they are less susceptible to inhibition by sodium chloride, the hyperactive variants are more effective than native human DNase I under physiological saline conditions, such as occur in pulmonary secretions and other biological fluids. Accordingly, hyperactive variants of human DNase I should be especially useful in treating patients having pulmonary secretions that comprise relatively large amounts of DNA.

It is therefore an object of the present invention to provide human DNase I variants that have greater DNA-hydrolytic activity than native human DNase I.

It is another object of the invention to provide nucleic acids encoding such hyperactive variants of human DNase I, recombinant vectors comprising such nucleic acids, recombinant host cells transformed with those nucleic acids or vectors, and processes for producing the human DNase I variants by means of recombinant DNA technology. The invention includes the use of such nucleic acids and vectors for in vivo or ex vivo gene therapy.

The invention also is directed to pharmaceutical compositions comprising the hyperactive variants of human DNase I, optionally together with a pharmaceutically acceptable excipient, as well as substantially purified antibodies that are capable of binding to such hyperactive variants.

The invention also is directed to methods of use of the hyperactive variants. Included are methods for reducing the viscoelasticity or viscous consistency of DNA-containing material in a patient, and for reducing or preventing formation of DNA-containing immune complexes in a patient, comprising administering a therapeutically effective dose of a hyperactive variant of human DNase I to the patient.

The invention is particularly directed to a method of treating a patient having a disease such as cystic fibrosis, chronic bronchitis, pneumonia, bronchiectasis, emphysema, asthma, or systemic lupus erythematosus, that comprises administering a therapeutically effective amount of a hyperactive variant of human DNase I to the patient.

These and other objects of the invention will be apparent to the ordinary artisan upon consideration of the specification as a whole.

BRIEF DESCRIPTION OF THE FIGURES

FIG. 1 shows the amino acid sequence of human mature DNase I (SEQ. ID. NO: 1). The numbers indicate the sequential position of amino acid residues within the sequence.

FIGS. 2–4 show data for the following variants:

Figure 4:
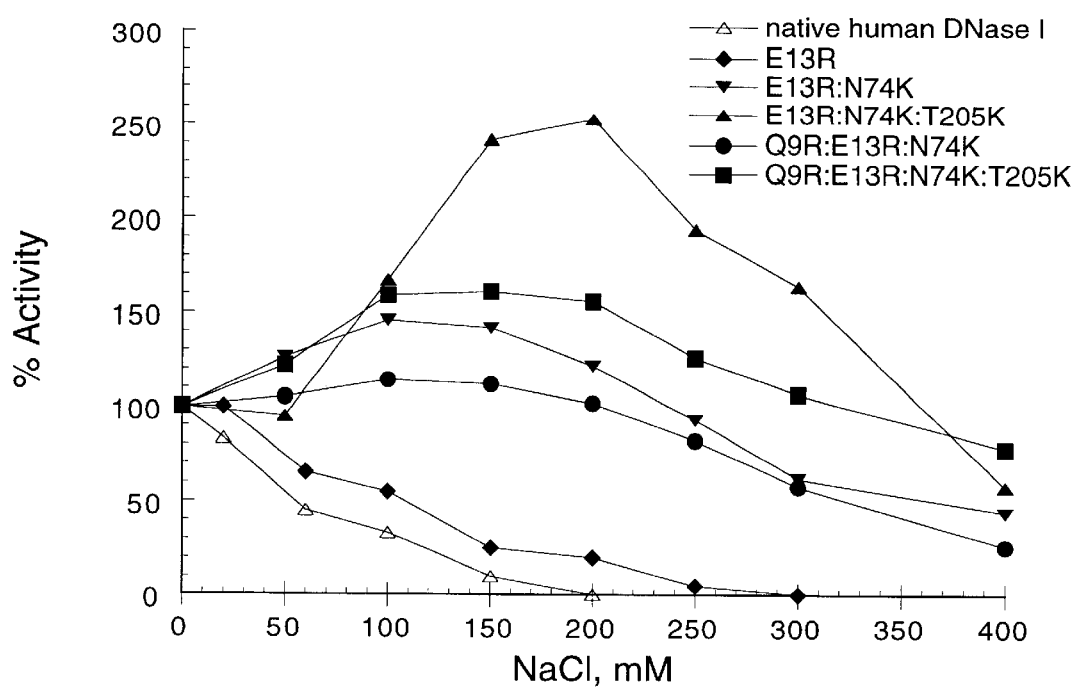

Q9R (SEQ. ID. NO: 2), E13K (SEQ. ID. NO: 3), E13R (SEQ. ID. NO: 4),

T14K (SEQ. ID. NO: 5), T14R (SEQ. ID. NO: 6), H44K (SEQ. ID. NO: 7),

H44R (SEQ. ID. NO: 8), N74K (SEQ. ID. NO: 9), N74R (SEQ. ID. NO: 10),

S75K (SEQ. ID. NO: 11), T205K (SEQ. ID. NO: 12), T205R (SEQ. ID. NO: 13),

E13R:N74K (SEQ. ID. NO. 14), Q9R:E13R:N74K (SEQ. ID. NO: 15),

E13R:N74K:T205K (SEQ. ID. NO: 16), Q9R:E13R:N74K:T205K (SEQ. ID. NO: 17).

FIG. 2 shows the activity of hyperactive variants of human DNase I determined in a supercoiled DNA digestion assay and a linear DNA digestion assay, as described in Example 3.

FIG. 3 shows the activity of hyperactive variants of human DNase I determined in a DNA hyperchromicity assay, as described in Example 3.

FIG. 4 shows the percent activity of native human DNase I and hyperactive variants of human DNase I determined in the presence of various concentrations of sodium chloride in a linear DNA digestion assay, as described in Example 3. Percent activity values are stated relative to the activity of each DNase I (native or variant) in the absence of added sodium chloride.

DETAILED DESCRIPTION

As used herein, the terms "human DNase I", "native human DNase I", and "wild-type DNase I" refer to the polypeptide having the amino acid sequence of human mature DNase I set forth in FIG. 1.

A "variant" or "amino acid sequence variant" of human DNase I is a polypeptide that comprises an amino acid sequence different from that of native human DNase I. Generally, a variant will possess at least 80% sequence identity, preferably at least 90% sequence identity, more preferably at least 95% sequence identity, and most preferably at least 98% sequence identity with native human DNase I. Percentage sequence identity is determined, for example, by the Fitch, et al., Proc. Nat. Acad. Sci. USA 80:1382–1386 (1983), version of the algorithm described by Needleman, et al., J. Mol. Biol. 48:443–453 (1970), after aligning the sequences to provide for maximum homology.

The terms "hyperactive variant", "human DNase I hyperactive variant", and "hyperactive variant of human DNase I" refer to a variant of native human DNase I that has increased DNA-hydrolytic activity as compared to native human DNase I.

"DNA-hydrolytic activity" refers to the enzymatic activity of native human DNase I or a variant of human DNase I in hydrolyzing substrate DNA to yield 5'-phosphorylated oligonucleotide end products. DNA-hydrolytic activity is readily determined by any of several different methods known in the art, including analytical polyacrylamide and agarose gel electrophoresis, hyperchromicity assay (Kunitz, J. Gen. Physiol. 33:349–362 (1950); Kunitz, J. Gen. Physiol. 33:363–377 (1950)), or methyl green assay (Kurnick, Arch. Biochem. 29:41–53 (1950); Sinicropi, et al., Anal. Biochem. 222:351–358 (1994)).

A human DNase I variant having "increased DNA-hydrolytic activity" is one that hydrolyzes DNA to a greater extent than native human DNase I as determined under comparable conditions. For example, if the linear DNA digestion assay described in Example 3 is used to determine DNA-hydrolytic activity, then a human DNase I variant having increased DNA-hydrolytic activity will be one having an activity greater than native human DNase I in the assay as determined under comparable conditions. In that assay, a hyperactive variant of human DNase I typically will have at least 50% greater DNA-hydrolytic activity than native human DNase, but hyperactive variants having upwards of 10-fold greater DNA-hydrolytic activity than native human DNase I also are readily produced, especially by altering multiple amino acid residues of the native human DNase I amino acid sequence (see e.g., FIG. 2).

"Mucolytic activity" refers to the reduction of viscoelasticity (viscosity) of sputum or other biological material, for example as observed upon treatment of the material with native human DNase I or a hyperactive variant of human DNase I. Mucolytic activity is readily determined by any of several different methods known in the art, including sputum compaction assay (PCT Patent Publication No. WO 94/10567, published May 11, 1994), assays using a torsion pendulum (Janmey, J. Biochem. Biophys. Methods 22:41–53 (1991), or other rheological methodologies.

"Polymerase chain reaction," or "PCR," generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridizing preferentially to a template nucleic acid.

"Cell," "host cell," "cell line," and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more DNA sequences, by means of enzymatic ligation or otherwise, in a configuration relative to one another such that the normal function of the sequences can be performed. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

Amino acids are identified herein by three-letter or single-letter designations, as follows:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

The present invention is based upon the study of structure, DNA-hydrolytic activity, and mucolytic activity of amino acid sequence variants of human DNase I. The hyperactive variants of the present invention have increased DNA-hydrolytic activity as compared to native human DNase I. The increased DNA-hydrolytic activity preferably is achieved by making mutations at and/or around those amino acid residues within native human DNase I that appear to affect the binding of DNA. Especially useful are mutations that introduce a basic amino acid residue (for example, lysine, arginine, or histidine) at one or more positions within the DNase I where the amino acid side chains are in close proximity to the negatively charged phosphate backbone of the bound DNA substrate, including, for example, at the positions of amino acid residues Gln9, Glu13, Thr14, His44, Asn74, Ser75, and Thr205 of native human DNase I (the number following the three-letter amino acid designation indicates the specific position of the amino acid residue within the FIG. 1 sequence).

There are a variety of ways in which one can make hyperactive variants of human DNase I. In one embodiment of this invention, a hyperactive variant is prepared by introducing either single or multiple amino acid substitutions, insertions, and/or deletions at or adjacent to (i.e., within about five amino acid residues of) those amino acid residues of native human DNase I that affect DNA binding. Some illustrative examples of such mutations are as follows: Q9R, E13K, E13R, T14K, T14R, H44K, H44R, N74K, N74R, S75K, T205K, T205R E13R:N74K, Q9R:E13R:N74K, E13R:N74K:T205K, Q9R:E13R:N74K:T205K (see FIGS. 2 and 3).

In a further embodiment of this invention, site-directed mutagenesis is used to introduce an amino acid residue at or adjacent to (i.e., within about five amino acid residues of) those amino acid residues of native human DNase I that are involved in DNA binding, which introduced residue is suitable for post-translational modification either biologically or chemically (see below). Means, et al., *Chemical Modification of Proteins* (Holden-Day, 1971); Glazer, et al., *Chemical Modification of Proteins: Selected Methods and Analytical Procedures* (Elsevier, 1975); Creighton, *Proteins*, pp.70–87 (W. H. Freeman, 1984); Lundblad, *Chemical Reagents for Protein Modification* (CRC Press, 1991). For example, a hyperactive variant of human DNase I may be produced by making post-translational modifications that increase the net positive charge at or adjacent to (i.e., within about five amino acid residues of) those amino acid residues of native human DNase I that are involved in DNA binding. For example, a cysteine residue may be introduced at or adjacent to a residue of native human DNase I that is involved in DNA binding. The free thiol of the cysteine residue then may be modified, for example, with a thiol-specific alkylating agent such as ethyleneimine which results in the formation of S-aminoethylcysteine, which carries a positive charge at neutral pH. An illustrative example of such mutations is H44C.

For convenience, substitutions, insertions, and/or deletions in the amino acid sequence of native human DNase I are usually made by introducing mutations into the corresponding nucleotide sequence of the DNA encoding native human DNase I, for example by site-directed mutagenesis. Expression of the mutated DNA then results in production of the variant human DNase I, having the desired (non-native) amino acid sequence.

Whereas any technique known in the art can be used to perform site-directed mutagenesis, e.g. as disclosed in Sambrook, et al., *Molecular Cloning: A Laboratory Manual*, Second Edition (Cold Spring Harbor Laboratory Press, New York (1989)), oligonucleotide-directed mutagenesis is the preferred method for preparing the human DNase I variants of this invention. This method, which is well known in the art (Zoller, et al., Meth. Enz. 100:4668–500 (1983); Zoller, et al., Meth. Enz. 154:329–350. (1987); Carter, Meth. Enz. 154:382–403 (1987); Kunkel, et al., Meth. Enzymol. 154:367–382 (1987); Horwitz, et al., Meth. Enz. 185:599–611 (1990)), is particularly suitable for making substitution variants, although it may also be used to conveniently prepare deletion and insertion variants.

The site-directed mutagenesis technique typically employs a phage vector that exists in both a single-stranded and double-stranded form. Typical vectors useful in site-directed mutagenesis include vectors such as the M13 phage, and plasmid vectors that contain a single-stranded phage origin of replication (Messing, et al., Meth. Enzymol. 101:20–78 (1983); Veira et al., Meth. Enzymol. 153:3–11 (1987); Short, et al., Nuc. Acids. Res. 16:7583–7600 (1988)). Replication of these vectors in suitable host cells results in the synthesis of single-stranded DNA that may be used for site-directed mutagenesis.

Briefly, in carrying out site-directed mutagenesis of DNA encoding native human DNase I (or a variant thereof), the DNA is altered by first hybridizing an oligonucleotide encoding the desired mutation to a single strand of the DNA. After hybridization, a DNA polymerase is used to synthesize an entire second strand, using the hybridized oligonucleotide as a primer, and using the single strand of the DNA as a template. Thus, the oligonucleotide encoding the desired mutation is incorporated in the resulting double-stranded DNA.

Oligonucleotides for use as hybridization probes or primers may be prepared by any suitable method, such as by purification of a naturally occurring DNA or by in vitro synthesis. For example, oligonucleotides are readily synthesized using various techniques in organic chemistry, such as described by Narang, et al., Meth. Enzymol. 68:90–98 (1979); Brown, et al., Meth. Enzymol. 68:109–151 (1979); Caruthers, et al., Meth. Enzymol. 154:287–313 (1985). The general approach to selecting a suitable hybridization probe or primer is well known. Keller, et al., *DNA Probes*, pp.11–18 (Stockton Press, 1989). Typically, the hybridization probe or primer will contain 10–25 or more nucleotides, and will include at least 5 nucleotides on either side of the sequence encoding the desired mutation so as to ensure that the oligonucleotide will hybridize preferentially at the desired location to the single-stranded DNA template molecule.

Of course, site-directed mutagenesis may be used to introduce multiple substitution, insertion, or deletion mutations into a starting DNA. If the sites to be mutated are located close together, the mutations may be introduced simultaneously using a single oligonucleotide that encodes all of the desired mutations. If, however, the sites to be mutated are located some distance from each other (separated by more than about ten nucleotides), it is more difficult to generate a single oligonucleotide that encodes all of the desired changes. Instead, one of two alternative methods may be employed.

In the first method, a separate oligonucleotide is generated for each desired mutation. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired variant. The first round is as described for introducing a single mutation. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

PCR mutagenesis (Higuchi, in *PCR Protocols*, pp.177–183 (Academic Press, 1990); Vallette, et al., Nuc. Acids Res. 17:723–733 (1989)) is also suitable for making the variants of human DNase I. Briefly, when small amounts of template DNA are used as starting material in a PCR, primers that differ slightly in sequence from the corresponding region in the template DNA can be used to generate relatively large quantities of a specific DNA fragment that differs from the template sequence only at the positions where the primers differ from the template. For introduction of a-mutation into a plasmid DNA, for example, the sequence of one of the primers includes the desired mutation and is designed to hybridize to one strand of the plasmid DNA at the position of the mutation; the sequence of the other primer must be identical to a nucleotide sequence within the opposite strand of the plasmid DNA, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. Wagner, et al., in *PCR Topics*, pp.69–71 (Springer-Verlag, 1991).

If the ratio of template to product amplified DNA is extremely low, the majority of product DNA fragments incorporate the desired mutation(s). This product DNA is used to replace the corresponding region in the plasmid that served as PCR template using standard recombinant DNA methods. Mutations at separate positions can be introduced simultaneously by either using a mutant second primer, or performing a second PCR with different mutant primers and ligating the two resulting PCR fragments simultaneously to the plasmid fragment in a three (or more)-part ligation.

Another method for preparing variants, cassette mutagenesis, is based on the technique described by Wells et al., Gene, 34:315–323 (1985). The starting material is the plasmid (or other vector) comprising the DNA sequence to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. The resulting plasmid contains the mutated DNA sequence.

The presence of mutation(s) in a DNA is determined by methods well known in the art, including restriction mapping and/or DNA sequencing. A preferred method for DNA sequencing is the dideoxy chain termination method of Sanger, et al., Proc. Nat. Acad. Sci. USA 72:3918–3921 (1979).

DNA encoding a human DNase I variant is inserted into a replicable vector for further cloning or expression. "Vectors" are plasmids and other DNAs that are capable of replicating within a host cell, and as such, are useful for performing two functions in conjunction with compatible host cells (a vector-host system). One function is to facilitate the cloning of the nucleic acid that encodes a human DNase I variant i.e., to produce usable quantities of the nucleic acid. The other function is to direct the expression of a human DNase I variant. One or both of these functions are performed by the vector in the particular host cell used for cloning or expression. The vectors will contain different components depending upon the function they are to perform.

To produce a human DNase I variant, an expression vector will comprise DNA encoding the variant, as described above, operably linked to a promoter and a ribosome binding site. The variant then is expressed directly in recombinant cell culture, or as a fusion with a heterologous polypeptide, preferably a signal sequence or other polypeptide having a specific cleavage site at the junction between the heterologous polypeptide and the human DNase I variant.

Prokaryotes (e.g., *E. coli,* and other bacteria) are the preferred host cells for the initial cloning steps of this invention. They are particularly useful for rapid production of large amounts of DNA, for production of single-stranded DNA templates used for site-directed mutagenesis, and for DNA sequencing of the variants generated. Prokaryotic host cells also may be used for expression of DNA encoding a human DNase I variant. Polypeptides that are produced in prokaryotic cells typically will be non-glycosylated.

In addition, the human DNase I variants of this invention may be expressed in eukaryotic host cells, including eukaryotic microbes (e.g., yeast) or cells derived from an animal or other multicellular organism (e.g., Chinese hamster ovary cells, and other mammalian cells), or in live animals (e.g., cows, goats, sheep)

Cloning and expression methodologies are well known in the art. Examples of prokaryotic and eukaryotic host cells, and expression vectors, suitable for use in producing the human DNase I variants of the present invention are, for example, those disclosed in Shak, PCT Patent Publication No. WO 90/07572 (published Jul. 12, 1990).

If prokaryotic cells or cells that contain substantial cell wall constructions are used as hosts, the preferred methods of transfection of the cells with DNA is the calcium treatment method described by Cohen et al., Proc. Natl. Acad. Sci. 69:2110–2114 (1972) or the polyethylene glycol method of Chung et al., Nuc. Acids. Res. 16:3580 (1988). If yeast are used as the host, transfection is generally accomplished using polyethylene glycol, as taught by Hinnen, *Proc. Natl. Acad. Sci.* U.S.A., 75: 1929–1933 (1978). If mammalian cells are used as host cells, transfection generally is carried out by the calcium phosphate precipitation method, Graham, et al., Virology 52:546 (1978), Gorman, et al., DNA and Protein Eng. Tech. 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding human DNase I variants. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties. Wong, et al., Science 228:810–815 (1985); Lee, et al., Proc. Nat Acad. Sci. USA 82:4360–4364 (1985); Yang, et al., Cell 47:3–10 (1986). Thus, transient expression systems are conveniently used for expressing the DNA encoding amino acid sequence variants of native human DNase I, in conjunction with assays to identify those variants that have increased DNA-hydrolytic activity.

A human DNase I variant preferably is secreted from the host cell in which it is expressed, in which case the variant is recovered from the culture medium in which the host cells are grown. In that case, it may be desirable to grow the cells in a serum free culture medium, since the absence of serum proteins and other serum components in the medium may facilitate purification of the variant. If it is not secreted, then the human DNase I variant is recovered from lysates of the host cells. When the variant is expressed in a host cell other than one of human origin, the variant will be completely free of proteins of human origin. In any event, it will be necessary to purify the variant from recombinant cell proteins in order to obtain substantially homogeneous preparations of the human DNase I variant. For therapeutic uses, the purified variant preferably will be greater than 99% pure (i.e., any other proteins will comprise less than 1% of the total protein in the purified composition)

Generally, purification of a human DNase I variant is accomplished by taking advantage of the differential physicochemical properties of the variant as compared to the contaminants with which it may be associated. For example, as a first step, the culture medium or host cell lysate is centrifuged to remove particulate cell debris. The human DNase I variant thereafter is purified from contaminant soluble proteins and polypeptides, for example, by ammonium sulfate or ethanol precipitation, gel filtration (molecular exclusion chromatography), ion-exchange chromatography, hydrophobic chromatography, immunoaffinity chromatography (e.g., using a column comprising anti-human DNase I antibodies coupled to Sepharose), tentacle cation exchange chromatography (Frenz, et al., PCT Patent Publication No. WO 93/25670, published Dec. 23, 1993), reverse phase HPLC, and/or gel electrophoresis.

Of course, one skilled in the art will appreciate that the purification methods that are used for native human DNase I may require some modification to be useful in purifying a human DNase I variant, to account for structural and other differences between the native and variant proteins. For example, in some host cells (especially bacterial host cells) the human DNase I variant may be expressed initially in an insoluble, aggregated form (referred to in the art as "refractile bodies" or "inclusion bodies") in which case it will be necessary to solubilize and renature the human DNase I variant in the course of its purification. Methods for solubilizing and renaturing recombinant protein refractile bodies are known in the art (see e.g., Builder, et al., U.S. Pat. No. 4,511,502).

In another embodiment of this invention, covalent modifications are made to a native or variant human DNase I protein to increase the DNA-hydrolytic activity of the protein or to affect another property of the protein (e.g., stability, biological half-life, immunogenicity). Such covalent modifications may be made instead of or in addition to the amino acid sequence substitution, insertion, and deletion mutations described above.

Covalent modifications may be introduced by reacting targeted amino acid residues of the native or variant human DNase I with an organic derivatizing agent that is capable of reacting with selected amino acid side-chains or N- or C-terminal residues. Suitable derivatizing agents and methods are well known in the art.

For example, cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high p$K_a$ of the guanidine functional group. Furthermore, these reagents may react with the groups of lysine as well as the arginine epsilon-amino group.

Carboxyl side groups (aspartyl or glutamyl) are selectively modified by reaction with carbodiimides (R'-N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Covalent coupling of glycosides to amino acid residues of a native or variant human DNase I protein may be used to modify or increase the number or profile of carbohydrate substituents, especially at or adjacent to those residues that are involved in DNA binding. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine; tyrosine, or tryptophan or (f) the amide group of glutamine. Suitable methods are described, for example in PCT Patent Publication No. WO 87/05330 (published Sep. 11, 1987), and in Aplin, et al., CRC Crit. Rev. Biochem., pp. 259–306 (1981).

The covalent attachment of agents such as polyethylene glycol (PEG) or human serum albumin to human DNase I variants may reduce immunogenicity and/or toxicity of the variant and/or prolong its half-life, as has been observed with other proteins. Abuchowski, et al., J. Biol. Chem. 252:3582–3586 (1977); Poznansky, et al., FEBS Letters 239:18–22 (1988); Goodson, et al., Biotechnology 8:343–346 (1990); Katre, J. Immunol. 144:209–213 (1990); Harris, *Polyethylene Glycol Chemistry* (Plenum Press, 1992).

In a further embodiment of this invention, a hyperactive variant of human DNase I will comprise one or more additional amino acid sequence mutations or other covalent modifications that causes the variant to have reduced binding affinity for actin. Examples of such mutations and covalent modifications that reduce actin binding are described in co-pending U.S. patent application Ser. No. 08/403,873 (which corresponds to International Patent Application No. PCT/US95/02366, filed Feb. 24, 1995). A hyperactive variant also may comprise an amino acid sequence mutation or other covalent modification that reduces the susceptibility of the variant to degradation by proteases (e.g., neutrophil elastase) that may be present in sputum and other biological materials.

The DNA-hydrolytic activity of the human DNase I variants prepared as described above are readily determined using assays and methods known in the art and as described herein. Any such variant having increased DNA-hydrolytic activity (as defined herein) is a hyperactive variant within the scope of this invention.

Antibodies to hyperactive variants of human DNase I are produced by immunizing an animal with a hyperactive variant or a fragment thereof, optionally in conjunction with an immunogenic polypeptide, and thereafter recovering antibodies from the serum of the immunized animals. Alternatively, monoclonal antibodies are prepared from cells of the immunized animal in conventional fashion. The antibodies also can be made in the form of chimeric (e.g., humanized) or single chain antibodies or Fab fragments, using methods well known in the art. Preferably, the antibodies will bind to the hyperactive variant but will not substantially bind to (i.e., cross react with) other DNase proteins (such as native human and bovine DNase I). The antibodies can be used in methods relating to the localization and activity of the hyperactive variant, for example, for detecting and measuring its levels in tissues or clinical samples. Immobilized antibodies are particularly useful in the detection of the hyperactive variant in clinical samples for diagnostic purposes, and in the purification of the hyperactive variant, for example from recombinant cell cultures.

The hyperactive variants of human DNase I that are provided by this invention are used-to reduce the viscoelasticity of DNA-containing material, including sputum, mucus, or other pulmonary secretions. Such variants are particularly useful for the treatment of patients with pulmonary disease who have abnormal viscous or inspissated secretions and conditions such as acute or chronic bronchial pulmonary disease, including infectious pneumonia, bronchitis or tracheobronchitis, bronchiectasis, cystic fibrosis, asthma, tuberculosis, and fungal infections. For such therapies, a solution or finely divided dry preparation of the hyperactive variant is instilled in conventional fashion into the airways (e.g., bronchi) or lungs of a patient, for example by aerosolization.

The hyperactive variants are also useful for adjunctive treatment of abscesses or severe closed-space infections in conditions such as empyema, meningitis, abscess, peritonitis, sinusitis, otitis, periodontitis, pericarditis, pancreatitis, cholelithiasis, endocarditis and septic arthritis, as well as in topical treatments in a variety of inflammatory and infected lesions such as infected lesions of the skin and/or mucosal membranes, surgical wounds, ulcerative lesions and burns. The hyperactive variant may improve the efficacy of antibiotics used in the treatment of such infections (e.g., gentamicin activity is markedly reduced by reversible binding to intact DNA).

Hyperactive variants of human DNase I will be useful for the treatment of systemic lupus erythematosus (SLE), a life-threatening autoimmune disease characterized by the production of diverse autoantibodies. DNA is a major antigenic component of the immune complexes. In this instance, the hyperactive human DNase I (native or variant) may be given systemically, for example by intravenous, subcutaneous, intrathecal, or intramuscular administration to the affected patient.

Hyperactive variants of human DNase I also will be useful for preventing the new development and/or exacerbation of respiratory infections, such as may occur in patients having cystic fibrosis, chronic bronchitis, asthma, pneumonia, or other pulmonary disease, or patients whose breathing is assisted by ventilator or other mechanical device, or other patients at risk of developing respiratory infections, for example post-surgical patients.

The hyperactive variants of the invention can be formulated according to known methods to prepare therapeutically useful compositions. A preferred therapeutic composition is a solution of a hyperactive variant in a buffered or unbuffered aqueous solution, and preferably is an isotonic salt solution such as 150 mM sodium chloride containing 1.0 mM calcium chloride at pH 7. These solutions are particularly adaptable for use in commercially-available nebulizers including jet nebulizers and ultrasonic nebulizers useful for administration directly into the airways or lungs of an affected patient.

In another embodiment, the therapeutic composition comprises a dry powder of the hyperactive variant, preferably prepared by spray-drying of a solution of the variant, essentially as described in co-pending U.S. patent application Ser. No. 08/364,074 (filed Dec. 27, 1994).

In a further embodiment, the therapeutic composition comprises cells actively producing a hyperactive variant of human DNase I. Such cells may be directly introduced into the tissue of a patient, or may be encapsulated within porous membranes which are then implanted in a patient, in either case providing for the delivery of the hyperactive variant into areas within the body of the patient in need of increased DNA-hydrolytic activity. For example, the patient's own cells could be transformed, either in vivo or ex vivo, with DNA encoding a hyperactive variant of human DNase I, and then used to produce the variant DNase I directly within the patient. This latter method is commonly referred to as gene therapy.

The therapeutically effective amount of a hyperactive variant of human DNase I will depend, for example, upon the amount of DNA in the material to be treated, the therapeutic objectives, the route of administration, and the condition of the patient. Accordingly, it will be necessary for the therapist to titer the dosage and modify the route of administration as required to obtain the optimal therapeutic effect. In view of its increased DNA-hydrolytic activity, the amount of the hyperactive variant required to achieve a therapeutic effect may be less than the amount of native human DNase I necessary to achieve the same effect under the same conditions. Generally, the therapeutically effective amount of the hyperactive variant will be a dosage of from about 0.1 μg to about 5 mg of the variant per kilogram of body weight of the patient, administered within pharmaceutical compositions, as described herein.

A hyperactive human DNase I variant optionally is combined with or administered in concert with one or more other pharmacologic agents used to treat the conditions listed above, such as antibiotics, bronchodilators, antiinflammatory agents, mucolytics (e.g. n-acetyl-cysteine), actin binding or actin severing proteins (e.g., gelsolin; Matsudaira et al., Cell 54:139–140 (1988); Stossel, et al., PCT Patent Publication No. WO 94/22465 (published Oct. 13, 1994)), protease inhibitors, gene therapy product (e.g., comprising the cystic fibrosis transmembrane conductance regulator (CFTR) gene, Riordan, et al., Science 245:1066–1073 (1989)), glucocorticoids, or cytotoxic agents.

In addition to providing hyperactive variants of human DNase I, the present invention also enables the production of hyperactive variants of other deoxyribonucleases, by making mutations in the amino acid sequences of such other deoxyribonucleases that are equivalent to the mutations disclosed herein for human DNase I. For example, hyperactive variants of the human LS-DNase that is described in co-pending U.S. patent application Ser. No. 08/597,078 (filed Feb. 5, 1996) may be prepared by introducing one or more of the mutations E13R, E13K, S14R, S14K, N44R, N44K, N76R, N76K, T77R, and T77K into the amino acid sequence of the native mature LS-DNase (which sequence and the numbering thereof are as shown in FIG. 2 of U.S. patent application Ser. No. 08/597,078).

The following examples are offered by way of illustration only and are not intended to limit the invention in any manner. All patent and literature references cited herein are expressly incorporated.

EXAMPLE 1

Mutagenesis of Human DNase I

E. coli strain CJ236 (BioRad Laboratories, Richmond, Calif. USA) was transformed with plasmid pRK.DNase.3 using the method of Chung et al. (Nuc. Acids. Res. 16:3580 (1988). The plasmid pRK.DNase.3 used in making the present invention is as described in PCT Patent Publication No. WO 90/07572 (published Jul. 12, 1990), except that the nucleotide sequence encoding the mature human DNase I is as shown in FIG. 1A of Shak, et al., Proc. Nat. Acad. Sci. 87:9188–9192 (1990). Transformed cells were plated on LB agar plates containing 50 μg/ml carbenicillin and grown overnight at 37° C. 2YT broth (5 ml) containing 50 μg/ml carbenicillin and 10 μl VCSM13 helper phage (Stratagene, La Jolla, Calif. USA) was inoculated with an individual colony from the agar plate and grown overnight at 37° C. with agitation. Single stranded DNA was isolated from this culture and used as template for subsequent mutagenesis.

Site-directed mutagenesis was accomplished using synthetic oligonucleotides according to the method of Kunkel, et al. (Meth. Enzymol. 154: 367–382 (1987). The mutagenic oligonucleotides were 27-mers having 12 exact base matches 5' to the mismatched codon and 12 exact base matches 3' to the mismatched codon. Following mutagenesis, single stranded DNA from individual clones was subjected to dideoxy sequencing (Sanger, et al., Proc. Nat. Acad. Sci. USA 74: 5463–5467 (1977)). DNA having variant nucleotide sequences then was transformed as described above into E. coli strain XL1 Blue MRF' (Stratagene). After plating and single colony isolation as before, individual colonies were used to inoculate. 0.5 liter LB broth containing 50 ug/ml carbenicillin. Following growth overnight with agitation at 37° C., the cells were harvested by centrifugation and the variant DNA (in the expression vector) was purified using Qiagen tip-500 columns (Qiagen Inc., Chatsworth, Calif. USA).

FIGS. 2 and 3 identify the different human DNase I variants that were made. In the figures and throughout the specification, the description of the amino acid substitution mutation(s) present in a DNase I variant is abbreviated by a first alphabetical letter, a number, and a second alphabetical letter. The first alphabetical letter is the single letter abbreviation of amino acid residue in native (wild-type) human mature DNase I, the number indicates the position of that residue in native human mature DNase I (numbering as shown in FIG. 1), and the second alphabetical letter is the single letter abbreviation of the amino acid residue at that position in the variant DNase I. For example, in the DNase I variant having a E13R mutation, the glutamic acid (E) residue at position 13 in native human mature DNase I has been replaced by an arginine (R) residue. Multiple mutations in a single variant are designated similarly, with a colon (:) separating each of the different mutations that are present in the variant. For example, the designation E13R:N74K indicates that the variant has a E13R mutation and a N74K mutation.

EXAMPLE 2

Expression of Human DNase I Variants

Human embryonic kidney 293 cells (ATCC CRL 1573, American Type Culture Collection, Rockville, Md. USA) were grown in serum containing media in 150 mm plastic Petri dishes. Log phase cells were transiently cotransfected with 22.5 μg purified variant DNA (prepared as described above) and 17 μg adenovirus DNA using the calcium phosphate precipitation method (Gorman, et al., DNA and Protein Eng. Tech. 2:3–10 (1990)). Approximately 16 hours after transfection, the cells were washed with 15 ml phosphate buffered saline and the media was changed to serum free media. Cell culture media was harvested from each plate at about 96 hours following the serum free media change. A total of approximately 25 ml of cell culture supernatant containing the DNase I variant was obtained in this way. The pool of culture supernatant from each plate was concentrated about 10-fold using Centriprep 10 concentrators. The concentration of DNase I protein in the concentrates was determined using a DNase I protein ELISA as described in co-pending U.S. patent application Ser. No. 08/403,873 (which corresponds to International Patent Application No. PCT/US95/02366, filed Feb. 24, 1995).

Culture supernatant containing native human DNase I was prepared by the same procedure as described above, except that the 293 cells were transiently transfected with plasmid pRK.DNase.3.

EXAMPLE 3

Biochemical Activities of Human DNase I Variants
I. Plasmid DNA Digestion Assays To determine the DNA-hydrolytic activity of human DNase I variants, two different plasmid digestion assays were used. The first assay ("supercoiled DNA digestion assay") measured the conversion of supercoiled double-stranded pBR322 plasmid DNA to relaxed (nicked), linear, and degraded forms. The second assay ("linear DNA digestion assay") measured the conversion of linear double-stranded pBR322 DNA to degraded forms.

Specifically, culture supernatants (prepared as described above, and diluted approximately 1:1000 before use) were added to 160 μl of solution containing 25 μg/ml of either supercoiled pBR322 DNA or EcoRI-digested linearized pBR322 DNA in 25 mM HEPES, pH 7.1, 100 μg/ml bovine serum albumin, 1 mM $MgCl_2$, 2.5 mM $CaCl_2$, 150 mM NaCl, and the samples were incubated at room temperature. At various times, aliquots of the reaction mixtures were removed and quenched by the addition of 25 mM EDTA, together with xylene cyanol, bromophenol blue, and glycerol. The integrity of the pBR322 DNA in the quenched samples was analyzed by electrophoresis of the samples on 0.8% weight/vol. agarose gels. After electrophoresis, the gels were stained with a solution of ethidium bromide and the DNA in the gels was visualized by ultraviolet light. The relative amounts of supercoiled, relaxed, and linear forms of pBR322 DNA were determined by scanning of the gels with a Molecular Dynamics Model 575 FluorImager and quantitating the amount of DNA in the bands of the gel that corresponded to those different forms.

The results of these assays are shown in FIG. 2. In the supercoiled DNA digestion assay, the overall activity of the human DNase I variants was measured as the initial rate of disappearance of supercoiled DNA (as a result of it being converted to relaxed (nicked), linear, or degraded DNA), normalized relative to the rate observed with native human DNase I ("relative nicking activity"). The ratio of linearized to relaxed forms of psR322 DNA also was determined relative to that observed with native human DNase I ("L/R ratio")). In the linear DNA digestion assay, the activity of the human DNase I variants was measured as the initial rate of disappearance of linear DNA (as a result of it being converted to degraded forms), normalized relative to the rate observed with native human DNase I ("relative linear DNA digestion activity"). In the supercoiled DNA digestion assay, native human DNase I had a supercoiled DNA nicking activity of 1200±43 mg DNA $min^{-1}$ $mg^{-1}$ DNase I (n=2), and gave a linear to relaxed product ratio of 0.010. In the linear DNA digestion assay, native human DNase I had a linear DNA digestion activity of 23±3 mg DNA $min^{-1}$ $mg^{-1}$ DNase I (n=6).

II. Hyperchromicity Assay

The DNA-hydrolytic activity of human DNase I variants also was determined using a hyperchromicity assay which is based on the increase in absorbance at 260 nm upon denaturation and depolymerization of DNA (Kunitz, J. Gen. Physiol. 33:349–362 (1950); Kunitz, a. Gen. Physiol. 33:363–377 (1950)).

In the hyperchromicity assay, culture supernatants (prepared as described above, and diluted approximately 1:2 to 1:50 before use) were added to 150 μl of solution containing 10 μg/ml to 600 μg/ml calf thymus DNA in 25 mM HEPES, pH 7.1, 1 mM $MgCl_2$, 2.5 mM $CaCl_2$, 150 mM NaCl, and the increase in absorbance at 260 nm was monitored with a spectrophotometer (Molecular Devices Spectra Max 250) for six minutes. Plots of activity versus DNA concentration were hyperbolic and the data were fit to the Michaelis-Menton equation to generate $K_m$ and $V_{max}$ kinetic values. FIG. 3 shows $1/K_m$, $V_{max}$, and $V_{max}/K_m$ values calculated for the human DNase I variants which are normalized relative to those of native human DNase I. In this assay, native human DNase I had a $K_m$ of 229±33 μg/ml DNA (n=6) and a $V_{max}$ of 168±18 $A_{260}$ units $min^{-1}$ $mg^{-1}$ DNase I (n=6).

III. Effect of Sodium Chloride on DNA-Hydrolytic Activity

The effect of sodium chloride on DNA-hydrolytic activity of several human DNase I variants was determined using the linear DNA digestion assay essentially as described above, except that sodium chloride was added to the reaction mixtures to a final concentration of 20 mM to 400 mM. FIG. 4 shows the percent activity of hyperactive variants and native human DNase I at various concentrations of sodium chloride, relative to their respective activities in the absence of added sodium chloride.

---

What is claimed is:

1. A human DNase I variant comprising an amino acid sequence having at least 90% identity with the amino acid sequence of native human DNase I (SEQ ID NO: 1) and a substitution at one or more amino acid residues corresponding to Gln9, Thr14, Asn74, Ser75, and Thr205 of native human DNase I.

2. The human DNase I variant of claim 1 comprising an amino acid sequence having at least 95% identity with the amino acid sequence of native human DNase I (SEQ ID NO: 1).

3. The human DNase I variant of claim 1 having an amino acid sequence that differs from the amino acid sequence of native human DNase I by the substitution of one amino acid for another at only a single position within SEQ ID NO: 1.

4. The human DNase I variant of claim 1 having an amino acid sequence that differs from the amino acid sequence of native human DNase I by the substitution of one amino acid for another at two or more positions within SEQ ID NO: 1.

5. A method for the treatment of a patient having a pulmonary disease or disorder comprising administering to the patient a therapeutically effective amount of a human DNase I variant according to claim 1.

6. The method of claim 5 wherein the disease or disorder is cystic fibrosis.

7. A method for the treatment of a patient having systemic lupus erythematosus comprising administering to the patient a therapeutically effective amount of a human DNase I variant according to claim 1.

8. A pharmaceutical composition comprising a human DNase I variant according to claim 1 and a pharmaceutically acceptable excipient.

9. The composition of claim 8 wherein the composition is in liquid form.

10. The composition of claim 8 wherein the composition is in powder form.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
         (A) LENGTH: 260 amino acids
         (B) TYPE: Amino Acid
         (D) TOPOLOGY: Linear (xi) SEQUENCE DESCRIPTION: SEQ ID NO:1:

```
Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
```

```
                    35                  40                  45
Thr Ala Val Gly Lys Leu Leu Asp Asn Leu Asn Gln Asp Ala Pro
                50                  55                  60
Asp Thr Tyr His Tyr Val Val Ser Glu Pro Leu Gly Arg Asn Ser
                65                  70                  75
Tyr Lys Glu Arg Tyr Leu Phe Val Tyr Arg Pro Asp Gln Val Ser
                80                  85                  90
Ala Val Asp Ser Tyr Tyr Tyr Asp Asp Gly Cys Glu Pro Cys Gly
                95                 1 00                 1 05
Asn Asp Thr Phe Asn Arg Glu Pro Ala Ile Val Arg Phe Phe Ser
               110                 115                 120
Arg Phe Thr Glu Val Arg Glu Phe Ala Ile Val Pro Leu His Ala
               125                 130                 135
Ala Pro Gly Asp Ala Val Ala Glu Ile Asp Ala Leu Tyr Asp Val
               140                 145                 150
Tyr Leu Asp Val Gln Glu Lys Trp Gly Leu Glu Asp Val Met Leu
               155                 160                 165
Met Gly Asp Phe Asn Ala Gly Cys Ser Tyr Val Arg Pro Ser Gln
               170                 175                 180
Trp Ser Ser Ile Arg Leu Trp Thr Ser Pro Thr Phe Gln Trp Leu
               185                 190                 195
Ile Pro Asp Ser Ala Asp Thr Thr Ala Thr Pro Thr His Cys Ala
               200                 205                 210
Tyr Asp Arg Ile Val Val Ala Gly Met Leu Leu Arg Gly Ala Val
               215                 220                 225
Val Pro Asp Ser Ala Leu Pro Phe Asn Phe Gln Ala Ala Tyr Gly
               230                 235                 240
Leu Ser Asp Gln Leu Ala Gln Ala Ile Ser Asp His Tyr Pro Val
               245                 250                 255
Glu Val Met Leu Lys
               260

(2) INFORMATION FOR SEQ ID NO:2:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:2:

Leu Lys Ile Ala Ala Phe Asn Ile Arg Thr Phe Gly Glu Thr Lys
 1               5                  10                  15
Met Ser Asn Ala Thr Leu Val Ser Tyr Ile Val Gln Ile Leu Ser
                20                  25                  30
Arg Tyr Asp Ile Ala Leu Val Gln Glu Val Arg Asp Ser His Leu
                35                  40                  45
Thr Ala Val Gly Lys Leu Leu Asp Asn Leu Asn Gln Asp Ala Pro
                50                  55                  60
Asp Thr Tyr His Tyr Val Val Ser Glu Pro Leu Gly Arg Asn Ser
                65                  70                  75
Tyr Lys Glu Arg Tyr Leu Phe Val Tyr Arg Pro Asp Gln Val Ser
                80                  85                  90
Ala Val Asp Ser Tyr Tyr Tyr Asp Asp Gly Cys Glu Pro Cys Gly
                95                 1 00                 1 05
Asn Asp Thr Phe Asn Arg Glu Pro Ala Ile Val Arg Phe Phe Ser
```

```
                    110                 115                 120
Arg Phe Thr Glu Val Arg Glu Phe Ala Ile Val Pro Leu His Ala
                    125                 130                 135

Ala Pro Gly Asp Ala Val Ala Glu Ile Asp Ala Leu Tyr Asp Val
                    140                 145                 150

Tyr Leu Asp Val Gln Glu Lys Trp Gly Leu Glu Asp Val Met Leu
                    155                 160                 165

Met Gly Asp Phe Asn Ala Gly Cys Ser Tyr Val Arg Pro Ser Gln
                    170                 175                 180

Trp Ser Ser Ile Arg Leu Trp Thr Ser Pro Thr Phe Gln Trp Leu
                    185                 190                 195

Ile Pro Asp Ser Ala Asp Thr Thr Ala Thr Pro Thr His Cys Ala
                    200                 205                 210

Tyr Asp Arg Ile Val Val Ala Gly Met Leu Leu Arg Gly Ala Val
                    215                 220                 225

Val Pro Asp Ser Ala Leu Pro Phe Asn Phe Gln Ala Ala Tyr Gly
                    230                 235                 240

Leu Ser Asp Gln Leu Ala Gln Ala Ile Ser Asp His Tyr Pro Val
                    245                 250                 255

Glu Val Met Leu Lys
                    260

(2) INFORMATION FOR SEQ ID NO:3:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:3:

Leu Lys Ile Ala Ala Phe Asn Ile Gln Thr Phe Gly Lys Thr Lys
  1                   5                  10                 15

Met Ser Asn Ala Thr Leu Val Ser Tyr Ile Val Gln Ile Leu Ser
                     20                  25                 30

Arg Tyr Asp Ile Ala Leu Val Gln Glu Val Arg Asp Ser His Leu
                     35                  40                 45

Thr Ala Val Gly Lys Leu Leu Asp Asn Leu Asn Gln Asp Ala Pro
                     50                  55                 60

Asp Thr Tyr His Tyr Val Val Ser Glu Pro Leu Gly Arg Asn Ser
                     65                  70                 75

Tyr Lys Glu Arg Tyr Leu Phe Val Tyr Arg Pro Asp Gln Val Ser
                     80                  85                 90

Ala Val Asp Ser Tyr Tyr Asp Asp Gly Cys Glu Pro Cys Gly
                     95                 1 00                1 05

Asn Asp Thr Phe Asn Arg Glu Pro Ala Ile Val Arg Phe Phe Ser
                    110                 115                 120

Arg Phe Thr Glu Val Arg Glu Phe Ala Ile Val Pro Leu His Ala
                    125                 130                 135

Ala Pro Gly Asp Ala Val Ala Glu Ile Asp Ala Leu Tyr Asp Val
                    140                 145                 150

Tyr Leu Asp Val Gln Glu Lys Trp Gly Leu Glu Asp Val Met Leu
                    155                 160                 165

Met Gly Asp Phe Asn Ala Gly Cys Ser Tyr Val Arg Pro Ser Gln
                    170                 175                 180

Trp Ser Ser Ile Arg Leu Trp Thr Ser Pro Thr Phe Gln Trp Leu
```

```
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
                260

(2) INFORMATION FOR SEQ ID NO:4:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:4:

Leu Lys Ile Ala Ala Phe Asn Ile Gln Thr Phe Gly Arg Thr Lys
 1                5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
                35                  40                  45

Thr Ala Val Gly Lys Leu Leu Asp Asn Leu Asn Gln Asp Ala Pro
                50                  55                  60

Asp Thr Tyr His Tyr Val Val Ser Glu Pro Leu Gly Arg Asn Ser
                65                  70                  75

Tyr Lys Glu Arg Tyr Leu Phe Val Tyr Arg Pro Asp Gln Val Ser
                80                  85                  90

Ala Val Asp Ser Tyr Tyr Tyr Asp Asp Gly Cys Glu Pro Cys Gly
                95                  1 00                 1 05

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
```

(2) INFORMATION FOR SEQ ID NO:5:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:5:

```
Leu Lys Ile Ala Ala Phe Asn Ile Gln Thr Phe Gly Glu Lys Lys
  1               5                  10                  15

Met Ser Asn Ala Thr Leu Val Ser Tyr Ile Val Gln Ile Leu Ser
                 20                  25                  30

Arg Tyr Asp Ile Ala Leu Val Gln Glu Val Arg Asp Ser His Leu
                 35                  40                  45

Thr Ala Val Gly Lys Leu Leu Asp Asn Leu Asn Gln Asp Ala Pro
                 50                  55                  60

Asp Thr Tyr His Tyr Val Val Ser Glu Pro Leu Gly Arg Asn Ser
                 65                  70                  75

Tyr Lys Glu Arg Tyr Leu Phe Val Tyr Arg Pro Asp Gln Val Ser
                 80                  85                  90

Ala Val Asp Ser Tyr Tyr Tyr Asp Asp Gly Cys Glu Pro Cys Gly
                 95                 100                 105

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
                260
```

(2) INFORMATION FOR SEQ ID NO:6:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:6:

```
Leu Lys Ile Ala Ala Phe Asn Ile Gln Thr Phe Gly Glu Arg Lys
  1               5                  10                  15
```

-continued

Met Ser Asn Ala Thr Leu Val Ser Tyr Ile Val Gln Ile Leu Ser
              20                  25                  30

Arg Tyr Asp Ile Ala Leu Val Gln Glu Val Arg Asp Ser His Leu
              35                  40                  45

Thr Ala Val Gly Lys Leu Leu Asp Asn Leu Asn Gln Asp Ala Pro
              50                  55                  60

Asp Thr Tyr His Tyr Val Val Ser Glu Pro Leu Gly Arg Asn Ser
              65                  70                  75

Tyr Lys Glu Arg Tyr Leu Phe Val Tyr Arg Pro Asp Gln Val Ser
              80                  85                  90

Ala Val Asp Ser Tyr Tyr Tyr Asp Gly Cys Glu Pro Cys Gly
              95                 1 00                1 05

Asn Asp Thr Phe Asn Arg Glu Pro Ala Ile Val Arg Phe Phe Ser
             110                 115                 120

Arg Phe Thr Glu Val Arg Glu Phe Ala Ile Val Pro Leu His Ala
             125                 130                 135

Ala Pro Gly Asp Ala Val Ala Glu Ile Asp Ala Leu Tyr Asp Val
             140                 145                 150

Tyr Leu Asp Val Gln Glu Lys Trp Gly Leu Glu Asp Val Met Leu
             155                 160                 165

Met Gly Asp Phe Asn Ala Gly Cys Ser Tyr Val Arg Pro Ser Gln
             170                 175                 180

Trp Ser Ser Ile Arg Leu Trp Thr Ser Pro Thr Phe Gln Trp Leu
             185                 190                 195

Ile Pro Asp Ser Ala Asp Thr Thr Ala Thr Pro Thr His Cys Ala
             200                 205                 210

Tyr Asp Arg Ile Val Val Ala Gly Met Leu Leu Arg Gly Ala Val
             215                 220                 225

Val Pro Asp Ser Ala Leu Pro Phe Asn Phe Gln Ala Ala Tyr Gly
             230                 235                 240

Leu Ser Asp Gln Leu Ala Gln Ala Ile Ser Asp His Tyr Pro Val
             245                 250                 255

Glu Val Met Leu Lys
             260

(2) INFORMATION FOR SEQ ID NO:7:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:7:

Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
              20                  25                  30

Arg Tyr Asp Ile Ala Leu Val Gln Glu Val Arg Asp Ser Lys Leu
              35                  40                  45

Thr Ala Val Gly Lys Leu Leu Asp Asn Leu Asn Gln Asp Ala Pro
              50                  55                  60

Asp Thr Tyr His Tyr Val Val Ser Glu Pro Leu Gly Arg Asn Ser
              65                  70                  75

Tyr Lys Glu Arg Tyr Leu Phe Val Tyr Arg Pro Asp Gln Val Ser
              80                  85                  90

```
Ala Val Asp Ser Tyr Tyr Tyr Asp Asp Gly Cys Glu Pro Cys Gly
             95                 1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Thr Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:8:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:8:

Leu Lys Ile Ala Ala Phe Asn Ile Gln Thr Phe Gly Glu Thr Lys
  1              5                  10                  15

Met Ser Asn Ala Thr Leu Val Ser Tyr Ile Val Gln Ile Leu Ser
             20                  25                  30

Arg Tyr Asp Ile Ala Leu Val Gln Glu Val Arg Asp Ser Arg Leu
             35                  40                  45

Thr Ala Val Gly Lys Leu Leu Asp Asn Leu Asn Gln Asp Ala Pro
             50                  55                  60

Asp Thr Tyr His Tyr Val Val Ser Glu Pro Leu Gly Arg Asn Ser
             65                  70                  75

Tyr Lys Glu Arg Tyr Leu Phe Val Tyr Arg Pro Asp Gln Val Ser
             80                  85                  90

Ala Val Asp Ser Tyr Tyr Tyr Asp Asp Gly Cys Glu Pro Cys Gly
             95                 1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165
```

```
Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Thr Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:9:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:9:

Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
            20                  25                  30

Arg Tyr Asp Ile Ala Leu Val Gln Glu Val Arg Asp Ser His Leu
            35                  40                  45

Thr Ala Val Gly Lys Leu Leu Asp Asn Leu Asn Gln Asp Ala Pro
            50                  55                  60

Asp Thr Tyr His Tyr Val Val Ser Glu Pro Leu Gly Arg Lys Ser
            65                  70                  75

Tyr Lys Glu Arg Tyr Leu Phe Val Tyr Arg Pro Asp Gln Val Ser
            80                  85                  90

Ala Val Asp Ser Tyr Tyr Tyr Asp Asp Gly Cys Glu Pro Cys Gly
            95                  1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Thr Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240
```

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:10:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:10:

Leu Lys Ile Ala Ala Phe Asn Ile Gln Thr Phe Gly Glu Thr Lys
  1               5                  10                  15

Met Ser Asn Ala Thr Leu Val Ser Tyr Ile Val Gln Ile Leu Ser
                 20                  25                  30

Arg Tyr Asp Ile Ala Leu Val Gln Glu Val Arg Asp Ser His Leu
                 35                  40                  45

Thr Ala Val Gly Lys Leu Leu Asp Asn Leu Asn Gln Asp Ala Pro
                 50                  55                  60

Asp Thr Tyr His Tyr Val Val Ser Glu Pro Leu Gly Arg Arg Ser
                 65                  70                  75

Tyr Lys Glu Arg Tyr Leu Phe Val Tyr Arg Pro Asp Gln Val Ser
                 80                  85                  90

Ala Val Asp Ser Tyr Tyr Tyr Asp Asp Gly Cys Glu Pro Cys Gly
                 95                 1 00                1 05

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
            260

(2) INFORMATION FOR SEQ ID NO:11:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:11:

```
Leu Lys Ile Ala Ala Phe Asn Ile Gln Thr Phe Gly Glu Thr Lys
  1               5                  10                  15

Met Ser Asn Ala Thr Leu Val Ser Tyr Ile Val Gln Ile Leu Ser
             20                  25                  30

Arg Tyr Asp Ile Ala Leu Val Gln Glu Val Arg Asp Ser His Leu
             35                  40                  45

Thr Ala Val Gly Lys Leu Leu Asp Asn Leu Asn Gln Asp Ala Pro
             50                  55                  60

Asp Thr Tyr His Tyr Val Val Ser Glu Pro Leu Gly Arg Asn Lys
             65                  70                  75

Tyr Lys Glu Arg Tyr Leu Phe Val Tyr Arg Pro Asp Gln Val Ser
             80                  85                  90

Ala Val Asp Ser Tyr Tyr Tyr Asp Asp Gly Cys Glu Pro Cys Gly
             95                 1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Thr Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:12:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:12:

Leu Lys Ile Ala Ala Phe Asn Ile Gln Thr Phe Gly Glu Thr Lys
  1               5                  10                  15

Met Ser Asn Ala Thr Leu Val Ser Tyr Ile Val Gln Ile Leu Ser
             20                  25                  30

Arg Tyr Asp Ile Ala Leu Val Gln Glu Val Arg Asp Ser His Leu
             35                  40                  45

Thr Ala Val Gly Lys Leu Leu Asp Asn Leu Asn Gln Asp Ala Pro
             50                  55                  60

Asp Thr Tyr His Tyr Val Val Ser Glu Pro Leu Gly Arg Asn Ser
             65                  70                  75
```

-continued

```
Tyr Lys Glu Arg Tyr Leu Phe Val Tyr Arg Pro Asp Gln Val Ser
             80                  85                  90

Ala Val Asp Ser Tyr Tyr Tyr Asp Asp Gly Cys Glu Pro Cys Gly
             95                 1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Lys Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260
```

(2) INFORMATION FOR SEQ ID NO:13:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:13:

```
Leu Lys Ile Ala Ala Phe Asn Ile Gln Thr Phe Gly Glu Thr Lys
 1               5                  10                  15

Met Ser Asn Ala Thr Leu Val Ser Tyr Ile Val Gln Ile Leu Ser
             20                  25                  30

Arg Tyr Asp Ile Ala Leu Val Gln Glu Val Arg Asp Ser His Leu
             35                  40                  45

Thr Ala Val Gly Lys Leu Leu Asp Asn Leu Asn Gln Asp Ala Pro
             50                  55                  60

Asp Thr Tyr His Tyr Val Val Ser Glu Pro Leu Gly Arg Asn Ser
             65                  70                  75

Tyr Lys Glu Arg Tyr Leu Phe Val Tyr Arg Pro Asp Gln Val Ser
             80                  85                  90

Ala Val Asp Ser Tyr Tyr Tyr Asp Asp Gly Cys Glu Pro Cys Gly
             95                 1 00                1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150
```

```
Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Arg Pro Thr His Cys Ala
            200                 205                 210

Tyr Asp Arg Ile Val Val Ala Gly Met Leu Leu Arg Gly Ala Val
            215                 220                 225

Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:14:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:14:

Leu Lys Ile Ala Ala Phe Asn Ile Gln Thr Phe Gly Arg Thr Lys
 1               5                  10                  15

Met Ser Asn Ala Thr Leu Val Ser Tyr Ile Val Gln Ile Leu Ser
            20                  25                  30

Arg Tyr Asp Ile Ala Leu Val Gln Glu Val Arg Asp Ser His Leu
            35                  40                  45

Thr Ala Val Gly Lys Leu Leu Asp Asn Leu Asn Gln Asp Ala Pro
            50                  55                  60

Asp Thr Tyr His Tyr Val Val Ser Glu Pro Leu Gly Arg Lys Ser
            65                  70                  75

Tyr Lys Glu Arg Tyr Leu Phe Val Tyr Arg Pro Asp Gln Val Ser
            80                  85                  90

Ala Val Asp Ser Tyr Tyr Tyr Asp Asp Gly Cys Glu Pro Cys Gly
            95                  1 00                 1 05

Asn Asp Thr Phe Asn Arg Glu Pro Ala Ile Val Arg Phe Phe Ser
            110                 115                 120

Arg Phe Thr Glu Val Arg Glu Phe Ala Ile Val Pro Leu His Ala
            125                 130                 135

Ala Pro Gly Asp Ala Val Ala Glu Ile Asp Ala Leu Tyr Asp Val
            140                 145                 150

Tyr Leu Asp Val Gln Glu Lys Trp Gly Leu Glu Asp Val Met Leu
            155                 160                 165

Met Gly Asp Phe Asn Ala Gly Cys Ser Tyr Val Arg Pro Ser Gln
            170                 175                 180

Trp Ser Ser Ile Arg Leu Trp Thr Ser Pro Thr Phe Gln Trp Leu
            185                 190                 195

Ile Pro Asp Ser Ala Asp Thr Thr Ala Thr Pro Thr His Cys Ala
            200                 205                 210

Tyr Asp Arg Ile Val Val Ala Gly Met Leu Leu Arg Gly Ala Val
            215                 220                 225
```

```
Val Pro Asp Ser Ala Leu Pro Phe Asn Phe Gln Ala Ala Tyr Gly
            230                 235                 240

Leu Ser Asp Gln Leu Ala Gln Ala Ile Ser Asp His Tyr Pro Val
            245                 250                 255

Glu Val Met Leu Lys
            260

(2) INFORMATION FOR SEQ ID NO:15:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:15:

Leu Lys Ile Ala Ala Phe Asn Ile Arg Thr Phe Gly Arg Thr Lys
  1               5                  10                  15

Met Ser Asn Ala Thr Leu Val Ser Tyr Ile Val Gln Ile Leu Ser
                 20                  25                  30

Arg Tyr Asp Ile Ala Leu Val Gln Glu Val Arg Asp Ser His Leu
                 35                  40                  45

Thr Ala Val Gly Lys Leu Leu Asp Asn Leu Asn Gln Asp Ala Pro
                 50                  55                  60

Asp Thr Tyr His Tyr Val Val Ser Glu Pro Leu Gly Arg Lys Ser
                 65                  70                  75

Tyr Lys Glu Arg Tyr Leu Phe Val Tyr Arg Pro Asp Gln Val Ser
                 80                  85                  90

Ala Val Asp Ser Tyr Tyr Tyr Asp Asp Gly Cys Glu Pro Cys Gly
                 95                 1 00                1 05

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Thr Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
                260

(2) INFORMATION FOR SEQ ID NO:16:

(i) SEQUENCE CHARACTERISTICS:
        (A) LENGTH: 260 amino acids
```

(B) TYPE: Amino Acid
        (D) TOPOLOGY: Linear (xi) SEQUENCE DESCRIPTION: SEQ ID NO:16:

Leu Lys Ile Ala Ala Phe Asn Ile Gln Thr Phe Gly Arg Thr Lys
 1               5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
                35                  40                  45

Thr Ala Val Gly Lys Leu Leu Asp Asn Leu Asn Gln Asp Ala Pro
                50                  55                  60

Asp Thr Tyr His Tyr Val Val Ser Glu Pro Leu Gly Arg Lys Ser
                65                  70                  75

Tyr Lys Glu Arg Tyr Leu Phe Val Tyr Arg Pro Asp Gln Val Ser
                80                  85                  90

Ala Val Asp Ser Tyr Tyr Tyr Asp Asp Gly Cys Glu Pro Cys Gly
                95                  1 00                 1 05

Asn Asp Thr Phe Asn Arg Glu Pro Ala Ile Val Arg Phe Phe Ser
                110                 115                 120

Arg Phe Thr Glu Val Arg Glu Phe Ala Ile Val Pro Leu His Ala
                125                 130                 135

Ala Pro Gly Asp Ala Val Ala Glu Ile Asp Ala Leu Tyr Asp Val
                140                 145                 150

Tyr Leu Asp Val Gln Glu Lys Trp Gly Leu Glu Asp Val Met Leu
                155                 160                 165

Met Gly Asp Phe Asn Ala Gly Cys Ser Tyr Val Arg Pro Ser Gln
                170                 175                 180

Trp Ser Ser Ile Arg Leu Trp Thr Ser Pro Thr Phe Gln Trp Leu
                185                 190                 195

Ile Pro Asp Ser Ala Asp Thr Thr Ala Lys Pro Thr His Cys Ala
                200                 205                 210

Tyr Asp Arg Ile Val Val Ala Gly Met Leu Leu Arg Gly Ala Val
                215                 220                 225

Val Pro Asp Ser Ala Leu Pro Phe Asn Phe Gln Ala Ala Tyr Gly
                230                 235                 240

Leu Ser Asp Gln Leu Ala Gln Ala Ile Ser Asp His Tyr Pro Val
                245                 250                 255

Glu Val Met Leu Lys
                260

(2) INFORMATION FOR SEQ ID NO:17:

(i) SEQUENCE CHARACTERISTICS:
        (A) LENGTH: 260 amino acids
        (B) TYPE: Amino Acid
        (D) TOPOLOGY: Linear (xi) SEQUENCE DESCRIPTION: SEQ ID NO:17:

Leu Lys Ile Ala Ala Phe Asn Ile Arg Thr Phe Gly Arg Thr Lys
 1               5                  10                  15

Met Ser Asn Ala Thr Leu Val Ser Tyr Ile Val Gln Ile Leu Ser
                20                  25                  30

Arg Tyr Asp Ile Ala Leu Val Gln Glu Val Arg Asp Ser His Leu
                35                  40                  45

Thr Ala Val Gly Lys Leu Leu Asp Asn Leu Asn Gln Asp Ala Pro

-continued

```
                    50                  55                  60
Asp Thr Tyr His Tyr Val Val Ser Glu Pro Leu Gly Arg Lys Ser
                65                  70                  75
Tyr Lys Glu Arg Tyr Leu Phe Val Tyr Arg Pro Asp Gln Val Ser
                80                  85                  90
Ala Val Asp Ser Tyr Tyr Tyr Asp Asp Gly Cys Glu Pro Cys Gly
                95                  1 00                1 05
Asn Asp Thr Phe Asn Arg Glu Pro Ala Ile Val Arg Phe Phe Ser
                110                 115                 120
Arg Phe Thr Glu Val Arg Glu Phe Ala Ile Val Pro Leu His Ala
                125                 130                 135
Ala Pro Gly Asp Ala Val Ala Glu Ile Asp Ala Leu Tyr Asp Val
                140                 145                 150
Tyr Leu Asp Val Gln Glu Lys Trp Gly Leu Glu Asp Val Met Leu
                155                 160                 165
Met Gly Asp Phe Asn Ala Gly Cys Ser Tyr Val Arg Pro Ser Gln
                170                 175                 180
Trp Ser Ser Ile Arg Leu Trp Thr Ser Pro Thr Phe Gln Trp Leu
                185                 190                 195
Ile Pro Asp Ser Ala Asp Thr Thr Ala Lys Pro Thr His Cys Ala
                200                 205                 210
Tyr Asp Arg Ile Val Val Ala Gly Met Leu Leu Arg Gly Ala Val
                215                 220                 225
Val Pro Asp Ser Ala Leu Pro Phe Asn Phe Gln Ala Ala Tyr Gly
                230                 235                 240
Leu Ser Asp Gln Leu Ala Gln Ala Ile Ser Asp His Tyr Pro Val
                245                 250                 255
Glu Val Met Leu Lys
                260
```